(12) United States Patent
Swencki-Underwood et al.

(10) Patent No.: US 8,338,171 B2
(45) Date of Patent: Dec. 25, 2012

(54) BABOON HOMOLOG OF HUMAN CD147

(75) Inventors: Bethany Swencki-Underwood, Radnor, PA (US); Michael Naso, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 80 days.

(21) Appl. No.: 12/855,214

(22) Filed: Aug. 12, 2010

(65) Prior Publication Data

US 2011/0052499 A1    Mar. 3, 2011

Related U.S. Application Data (60) Provisional application No. 61/238,288, filed on Aug. 31, 2009.

(51) Int. Cl.
   C12P 21/04    (2006.01)
   C12P 21/06    (2006.01)
   C12N 1/00     (2006.01)
   C12N 15/00    (2006.01)
   C07H 21/04    (2006.01)
   C07K 14/47    (2006.01)

(52) U.S. Cl. ...... 435/325; 435/69.1; 435/71.1; 435/243; 435/320.1; 435/70.1; 536/23.5; 530/350

(58) Field of Classification Search ..................... None
   See application file for complete search history.

(56) References Cited

FOREIGN PATENT DOCUMENTS

| WO | WO 02/13763 | * | 2/2002 |
|---|---|---|---|
| WO | WO 2010/036460 A2 | | 4/2010 |

OTHER PUBLICATIONS

Kasinerk, W. et al., J. Immunol. 149(3), pp. 847-854 (1992).
Ellis, Cancer Research, 49, pp. 3385-3391 (1989).
Biswas et al., Cancer Research, 55: pp. 434-439 (1995).
Xu et al., Hepatology 45, pp. 269-276 (2007).
Deeg et al., Blood, 98, pp. 2052-2058 (2001).
Yu et al., J. Biol. Chem., 283(26), pp. 18056-18065 (2008).
Protein Translations of Life; Basigin Isoform 2 Precursor [*Homo sapiens*], NCBI Accession No. NP_940991, 2009.
Poustka et al, Proteins Translations of Life; Hypothetical Protein [*Pongo abelii*], NCBI Accession No. CAH90688, 2008.
Protein Translations of Life, Predicted: similar to basigin isoform 1 [*Macaca mulatta*], NCBI Reference No. XP_001117081, 2006.

\* cited by examiner

*Primary Examiner* — Marianne P Allen
(74) *Attorney, Agent, or Firm* — Kenneth J. Dow (57) ABSTRACT

Polynucleotide sequences encoding a baboon homolog of human CD147 and polypeptides obtainable form the polynucleotides and uses are disclosed.

5 Claims, 5 Drawing Sheets

```
       M   A   A   K   L   F   V   L   L   G   L   A   L   L   G   A   H   G   A   S
  1    ATGGCGGCTA AGCTGTTCGT GCTGCTGGGT TTGGCGCTGC TGGGCGCCCA CGGAGCCTCC

G   A   A   G   T   V   S   T   S   V   E   N   I   G   S   K   T   L   L   T
 61    GGGGCTGCCG GCACAGTCTC CACTTCCGTA GAAAACATTG GCTCGAAGAC ACTCCTGACC

C   S   L   N   D   S   S   T   E   V   T   G   H   R   W   L   K   G   G   A
121    TGCTCCTTGA ACGACAGCTC CACAGAGGTC ACCGGGCACC GCTGGCTGAA AGGTGGCGCG

V   L   K   E   D   T   L   P   G   Q   K   T   D   F   E   V   D   S   D   D
181    GTGCTGAAGG AGGACACGCT GCCCGGCCAG AAAACGGACT TCGAGGTGGA CTCCGACGAC

L   S   G   E   Y   S   C   V   F   L   P   E   P   T   G   R   A   D   I   Q
241    CTCTCGGGAG AGTACTCCTG CGTCTTCCTC CCCGAGCCCA CGGGCAGGGC CGACATCCAG

L   D   A   L   L   S   G   A   P   R   V   K   A   V   K   S   S   E   H   V
301    CTCGACGCCC TCCTGTCAGG CGCCCCCAGA GTGAAGGCTG TGAAGTCGTC AGAACACGTC

S   E   G   E   T   A   V   L   A   C   K   S   E   S   L   P   P   V   T   N
361    AGCGAGGGGG AGACGGCCGT GCTGGCCTGC AAGTCAGAGT CCCTGCCCCC CGTCACCAAC

W   V   W   Y   K   I   T   D   S   G   D   Q   V   I   V   N   G   S   Q   G
421    TGGGTCTGGT ACAAGATAAC TGACTCTGGG GACCAGGTCA TCGTGAACGG CTCCCAGGGC

R   F   F   V   S   S   S   Q   S   R   S   E   L   R   I   E   N   L   N   M
481    AGGTTCTTCG TGAGTTCCTC GCAGAGCCGG TCGGAGCTAC GCATCGAGAA CCTGAACATG

E   A   D   P   G   K   Y   A   C   N   G   T   S   S   E   G   T   D   Q   A
541    GAGGCCGACC CCGGCAAGTA CGCGTGCAAT GGCACCAGCT CCGAGGGCAC CGACCAGGCC

V   V   T   L   R   V   R   S   H   L   A   A   L   W   P   F   L   G   I   V
601    GTGGTCACTC TCCGCGTGCG TAGCCACCTG GCCGCCCTTT GGCCCTTCCT GGGCATCGTG

A   E   V   L   V   T   I   I   F   I   Y   E   K   R   R   K   P   E
661    GCTGAGGTGC TGGTGCTGGT CACCATCATC TTCATCTATG AAAAGCGCCG GAAGCCCGAG

D   V   L   D   D   D   A   G   S   A   P   L   K   S   T   G   Q   H   L
721    GACGTCCTGG ATGATGACGA CGCGGGCTCT GCTCCCCTGA AGAGCACTGG GCAGCACCTG

N   D   K   G   K   K   V   R   Q   R   N   S   S
781    AACGACAAAG GCAAGAAAGT CCGACAGAGG AACTCCTCCT AG
```

Fig. 3

```
baboon CD147    (1)
ATGGCGGCTAAGCTGTTCGTGCTGCTGGGTTTGGCGCTGCTGGGCGCCCACGGAGCCTCCGGCGCTGCCG
  human CD147    (1)
ATGGCGGCTGCGCTGTTCGTGCTGCTGGGATTCGCGCTGCTGGGCACCCACGGAGCCTCCGGCGCTGCCG baboon CD147   (71)
GCACAGTCTCCACTTCGTAGAAAACATTGGCTCGAAGACACTCCTGACCTGCTCCTTGAACGACAGCTC
  human CD147   (71)
GCACAGTCTTCACTACCGTAGAAGACCTTGGCTCCAAGATACTTCTCACCTGCTCCTTGAATGACAGCGC baboon CD147  (141)
CACAGAGGTCACCGGCACCGCTGGCTGAAAGGTGGCGCGGTGCTGAACGAGGACACGCTGCCCGGCCAG
  human CD147  (141)
CACAGAGGTCACAGGGCACCGCTGGCTGAAGGGGGCGGTGGTGCTGAAGGAGGACGCGCTGCCCGGCCAG baboon CD147  (211)
AAAACGGACTTCGAGGTGGACTCCGACGACCTCTCGGAGAGTACTCCTGCGTCTTCCTCCCCGAGCCCA
  human CD147  (211)
AAAACGGAGTTCAAGGTGGACTCCGACGACCAGTGGGGAGAGTACTCCTGCGTCTTCCTCCCCGAGCCCA baboon CD147  (281)
CGGGCAGGGCCGACATCCAGCTCGACGCCCTCCTGTCAGGCGCCCCCAGAGTGAAGGCTGTGAAGTCGTC
  human CD147  (281) TGGGCACGGCCAACATCCAGCTCCACG--GGCCT--------CCC--
AGAGTGAAGGCTGTGAAGTCGTC baboon CD147  (351)
AGAACACGTCAGCGAGGCGGAGAACGGCCGTGCTGGCCCTGCAAGTCAGAGTCCCTGCCCCCCGTCACCAAC
  human CD147  (339)
AGAACACATCAACGAGGGGGAGACGGCCATGCTGGTCTGCAAGTCAGAGTCCGTGCCACCTGTCACTGAC baboon CD147  (421)
TGGGTCTGGTACAAGATAACTGACTCTGGGGACCACGTCATCGTGAACGGCTCCCAGGGCACGTTCTTCG
  human CD147  (409)
TGGGCCTGGTACAAGATCACTGACTCTGAGGACAAGGCCCTTATGAACGGCTCCGAGAGCAGGTTCTTCG baboon CD147  (491)
TGAGTTCCTCGCAGAGCCGGTCGGAGCTACGCATCGAGAACCTGAACATGGAGGCCGACCCCGGCAAGTA
  human CD147  (479)
TGAGTTCCTCGCAGGGCCGGTCAGAGCTACACAATTGAGAACCTGAACATGGAGGCCGACCCCGGCCAGTA baboon CD147  (561)
CGCCGTGCAATGGCACCAGCTCCGAGGGCACCGACCAGGCCGTGGTCACTCTCCGGCGTGCGTAGCCACCTG
  human CD147  (549)
CCGGTGCAACGGCACCAGCTCCAAGGGCTCCGACCAGGCCATCATCACGCTCCGGCGTGCGCAGGCACCTG
```

*Fig. 3 cont'd.* baboon CD147   (631)
GCCGCCCTTTGGCCCTTCCTGGGCATCGTGGCTGAGGTGCTGGTGCTGGTCACCATCATCTTCATCTATG human CD147   (619)
GCCGCCCTCTGGCCCTTCCTGGGCATCGTGGCTGAGGTGCTGGTGCTGGTCACCATCATCTTCATCTACG baboon CD147   (701)
AGAAGCGTCGGAAGCCCGAGGACGTCCTGGATGATGACGACGCGGGCTCTGCTCCCCTGAAGAGCACTGG human CD147   (689)
AGAAGCGCCGGAAGCCCGAGGACGTCCTGGATGATGACGACGCCGGCTCTGCACCCCTGAAGAGCAGCGG baboon CD147   (771)  GCAGCACCTGAACGACAAAGGCAAGAAAGTCCGACAGAGGAACTCCTCCTAG human CD147   (759)  GCAGCACCAGAATGACAAAGGCAAGAACGTCCGCCAGAGGAACTCTTCCTGA

FIG. 4

```
                        1                                                  50
Baboon CD147    (1)  MAAKLFVLLGLALLGAHGASGAAGTVSTSVENIGSKTLLTCSLNDSSTEV
  Cyno CD147    (1)  MAAALFVLLGLALLGAHGAYGAAGTVSTSVENIGSKTLLTCSLNDSSTEV
 human CD147    (1)  MAAALFVLLGFALLGTHGASGAAGTVFTTVEDLGSKILLTCSLNDSATEV
Orangutan CD147 (1)  MAAALFVLLGFALLGAHGASGAAGTVSTSIETLGSKTLLTCFLNDSTTEV 51                                                 100
Baboon CD147   (51)  TGHRWLKGGAVLKEDTLPGQKTDFEVDSDDLSGEYSCVFLPEPTGRADIQ
  Cyno CD147   (51)  TGHRWLKGGAVLKEDTLPGQKTDFEVDSDDLGGEYSCVFLPEPTGRADIQ
 human CD147   (51)  TGHRWLKGGVVLKEDALPGQKTEFKVDSDDQWGEYSCVFLPEPMGTANIQ
Orangutan CD147 (51) TGHRWLKGGVVLKEDKLPDRKTDFEVDSDDHWEEYSCVFLPEPTGRADFQ 101                                                 150
Baboon CD147  (101)  LDA|LLSGA|PRVKAVKSSEHVSEGETAVLACKSESLPPVTNWVWYKITDSG
  Cyno CD147  (101)  LDA|VLSGA|PRVKAVKSSEHVSEGETAVLACKSESLPPVTTWVWYKITDSG
 human CD147  (101)  LHG|----P|PRVKAVKSSEHINEGETAMLVCKSESVPPVTDWAWYKITDSE
Orangutan CD147(101) LHG|----P|PRVKAVKSSEHINEGETAVLACKSESVPPVTDWVWYKITDSG 151                                                 200
Baboon CD147  (151)  DQVIVNGSQGRFFVSSSQSRSELRIENLNMEADPGKYACNGTSSEGTDQA
  Cyno CD147  (151)  DQVIVNGSQGRFFVSSSQGRSELRIENLNMEADPGKYACNGTSSEGTDQA
 human CD147  (147)  DKALMNGSESRFFVSSSQGRSELHIENLNMEADPGQYRCNGTSSKGSDQA
Orangutan CD147(147) DQVIMNGSESRFFVSSSQGRSELHIENLNMEADPGQYRCNGTSSEGTDQA 201                                                 250
Baboon CD147  (201)  VVTLRVRSHLAALWPFLGIVAEVLVLVTIIFIYEKRRKPEDVLDDDDAGS
  Cyno CD147  (201)  TVTLRVRSHLAALWPFLGIVAEVLVLVTIIFIYEKRRKPEDVLDDDDAGS
 human CD147  (197)  IITLRVRSHLAALWPFLGIVAEVLVLVTIIFIYEKRRKPEDVLDDDDAGS
Orangutan CD147(197) VITLRVRSHLAALWPFLGIVAEVLVLVTIIFIYEKRRKPEDVLDDDDAGS 251             273
Baboon CD147  (251)  APLKSTGQHLNDKGKKVRQRNSS
  Cyno CD147  (251)  APLKSTGQHLNDKGKKVRQRNSS
 human CD147  (247)  APLKSSGQHQNDKGKNVRQRNSS
Orangutan CD147(247) APLKSSGQHQNDKDKNVRQRNSS
```

BABOON HOMOLOG OF HUMAN CD147

This application claims priority to U.S. Provisional Application Ser. No. 61/238,288, filed on Aug. 31, 2009.

BACKGROUND OF THE INVENTION

1. Field of the Invention

The present invention relates to a homolog of human CD147 discovered in baboon tissue and its uses.

2. Description of the Related Art

EMMPRIN (extracellular matrix metalloproteinase inducer), also called basigin, leukocyte antigen M6, or CD147, is a member of the immunoglobulin superfamily. CD147 is a transmembrane glycoprotein, containing an extracellular Ig-like C2-type domain followed by an Ig-like V-type domain. CD147 is present on the surface of tumor cells and stimulates the production of matrix metalloproteinases (MMPs) and VEGF. Additionally, the mature protein forms homodimers and multimers in its native state.

The cDNA for human CD147 was isolated from peripheral blood leukocytes, and was found to be 810 bp in length (Kasinrerk, W. et al., 1992, J. Immunol. 149(3):847-54). The 269 amino acid polypeptide is now known as isoform 2 (Swissprot P35613-2) and is missing residues 24-139 of isoform 1. The 385 amino acid splice variant knows as isoform 1 is expressed only in the retina (Hanna, S. M. et al., 2003, BMC Biochem. 4:17). Other mRNA transcripts, but not proteins, have been reported.

As a protein involved in extracellular matrix remodeling, a process involved in cancer metastasis and wound healing, CD147 is of interest as a therapeutic drug target. For example, Centocor (co-pending application U.S. Ser. No. 61/100,848) and others (Ellis, 1989 Cancer Res 49:3385-91; Biswas et al. Cancer Research 55, 434-439, 1995; Xu, et al. (2007) Hepatology 45: 269-276) have generated neutralizing antibodies against human CD147. The use of a murine an anti-CD147 IgM Mab, CBL1, in human GvHD was reported (Deeg et al. 2001 Blood 98:2052-8).

A need in the art exists to improve current toxicological testing strategies through testing of closely related animal species with human or surrogate biologic proteins. As part of the characterization effort, it is critical to demonstrate reactivity of any therapeutic candidates against the orthologous proteins from available toxicology species, such as baboon.

SUMMARY OF THE INVENTION

The invention provides *Papio hamadryas* (Baboon) polynucleotides and polypeptides. One aspect of the invention is an isolated polynucleotide comprising a polynucleotide having the sequence shown in SEQ ID NO: 3 or a complementary sequence, fragment or variant thereof.

Another aspect of the invention is an isolated polypeptide comprising a polypeptide having the sequence shown in SEQ ID NO: 4 or a fragment thereof.

In another embodiment, the invention includes vectors and host cells comprising the polynucleotide having the sequence shown in SEQ ID NO: 3 or a complementary sequence, fragment or variant thereof.

In another embodiment, the invention includes antibodies generated using the polynucleotide having the sequence shown in SEQ ID NO: 3 or a complementary sequence, fragment or variant thereof or expressed or isolated polypeptides encoded thereby.

In another embodiment, the polynucleotides, polypeptides, or antibody generated therefrom is used to test the effects of modulating CD147 in an *Papio* spp baboon or a closely related species of the invention.

BRIEF DESCRIPTION OF THE SEVERAL VIEWS OF THE DRAWING

FIG. 4 shows the polypeptide sequence alignment of baboon, cyno, human, and orangutan CD147 noting the region linking the C2-like immunoglobulin region and the V-like region is longer (5 residues instead of 1) in the baboon and cyno proteins.

BRIEF DESCRIPTION OF THE SEQUENCE LISTING

| SEQ ID NO: | Description |
| --- | --- |
| 1 | Human CD147 Isoform 2 |
| 2 | Primer |
| 3 | Primer |
| 4 | cDNA encoding baboon CD147 |
| 5 | Translated baboon CD147 |
| 6 | cDNA encoding human CD147 isoform 2 |
| 7 | Predicted Cyno CD147 |
| 8 | Hypothetical Orangutan CD147 |

DETAILED DESCRIPTION OF THE INVENTION

All publications, including but not limited to patents and patent applications, cited in this specification are herein incorporated by reference as though fully set forth.

ABBREVIATIONS

Cyno=Cynomolgus monkey (*Macaca fascicularis*); ECD=extracellular domain; CD147=extracellular matrix metalloproteinase inducer; MMP=matrix metalloproteinase; VEGF=vascular endothelial growth factor; spp=species;

Definitions

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426, and Huston et al. (1988) Proc. Natl. Acad Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296(1):57-86).

The term "CD147" is used herein to mean "Extracellular Matrix Metalloprotein Inducer", CD147, the product of the human basigin (bsg) gene, human leukocyte activation antigen M6, the species homologue of rat OX-47, mouse basigin, and chicken HT7 molecule, tumor cell-derived collagenase stimulatory factor, neurothelin and include all of the variants, isoforms and species homologs of CD147. Accordingly, the antibodies of the invention may, in certain cases, cross-react with CD147 from species other than human. In other cases, the antibodies may be completely specific for human CD147 and not exhibit species or other types of cross-reactivity.

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence. Having either a first polynucleotide strand sequence or the antiparallel strand sequence allows immediate recognition of the complimentary sequence of one for the other.

The term "polynucleotide" means a molecule comprising a chain of nucleotides covalently linked by a sugar-phosphate backbone or other equivalent covalent chemistry. Double and single stranded DNAs and RNAs are typical examples of polynucleotides. The utility of polynucleotide sequences is their ability to replicate or be replicated in systems using polymerases and be transcribed by ribosomal systems into polypeptides.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "polypeptide" means a molecule that comprises amino acid residues linked by a peptide bond to form a polypeptide. Small polypeptides of less than 50 amino acids may be referred to as "peptides". Polypeptides may also be referred as "proteins."

Overview

The human bsg gene product, CD147, known as CD147 isoform II (NCBI Accession No. NP_940991) is a propolypeptide 269 amino acids in length (SEQ ID NO: 1, FIG. 4), having a signal peptide 21, an 186 aa extracellular domain (residues 22-207), a transmembrane domain from residues 208-228, and an intracellular domain from residue 229 to the C-terminal residue, 269. According to the curated NCBI record, the extracellular domain (ECD) is comprised of two immunoglobulin-like domains: a C2-type domain from residue 22 to 103 and a V-like domain from residue 105-199. There are three potential N-glycosylation sites, at residue 44, 152 and 186; and two intramolecular disulfide bonds. The interaction between domains or between molecules, such as homodimer formation, and the relationship between domain structures and bioactivity remains an active area of CD147 investigtion.

Phylogenetic classification places the primates as the highest order of mammals. Included among primates are humans and the nonhuman primates, the apes, monkeys, lemurs, tree-shrews, lorises, aye-ayes, pottos, bush babies and tarsiers. The New World monkeys include the capuchin, howler and squirrel monkeys, and the catarrhines include the Cercopithecidae (Old World monkeys such as baboons and macaques) and the apes. Cercopithecidae, Homimidae (including humans and great apes), and Hylobatidae (gibbons) make up a suborder or "clade" within the order of primates, called Catarrhini. The macaque genus, which belongs to the Old World monkeys, includes cynomolgus monkey or "cyno" (*Macaca fascicularis*) and rhesus monkey (*Macaca mulatto*), often used in pharmaceutical and vaccine testing. The Homimidae (Hominids, also known as great apes) form a taxonomic family, including four extant genera: chimpanzees, gorillas, humans and orangutans. From these classifications, it would be expected that the baboons and cynomolgus monkey would be genetically more similar than baboons and human. A hypothetical orthologue protein from Sumatran orangutan (*Pongo abelli*) is known, NCBI Accession No. CAH90688) as well as a predicted rhesus sequence for an orthologue of human isoform I (XP_001117081). It could not be predicted, however, whether baboon or Cynomolgus monkey CD147 was more similar to human CD147.

The present invention provides isolated baboon (*Papio hamadryas*) CD147 polynucleotides, vectors comprising these polynucleotides, isolated host cells, polypeptides obtainable from expression of these polynucleotides, methods for expressing the polypeptides of the invention, and methods of using the polynucleotides and polypeptides of the invention.

Figure 3:
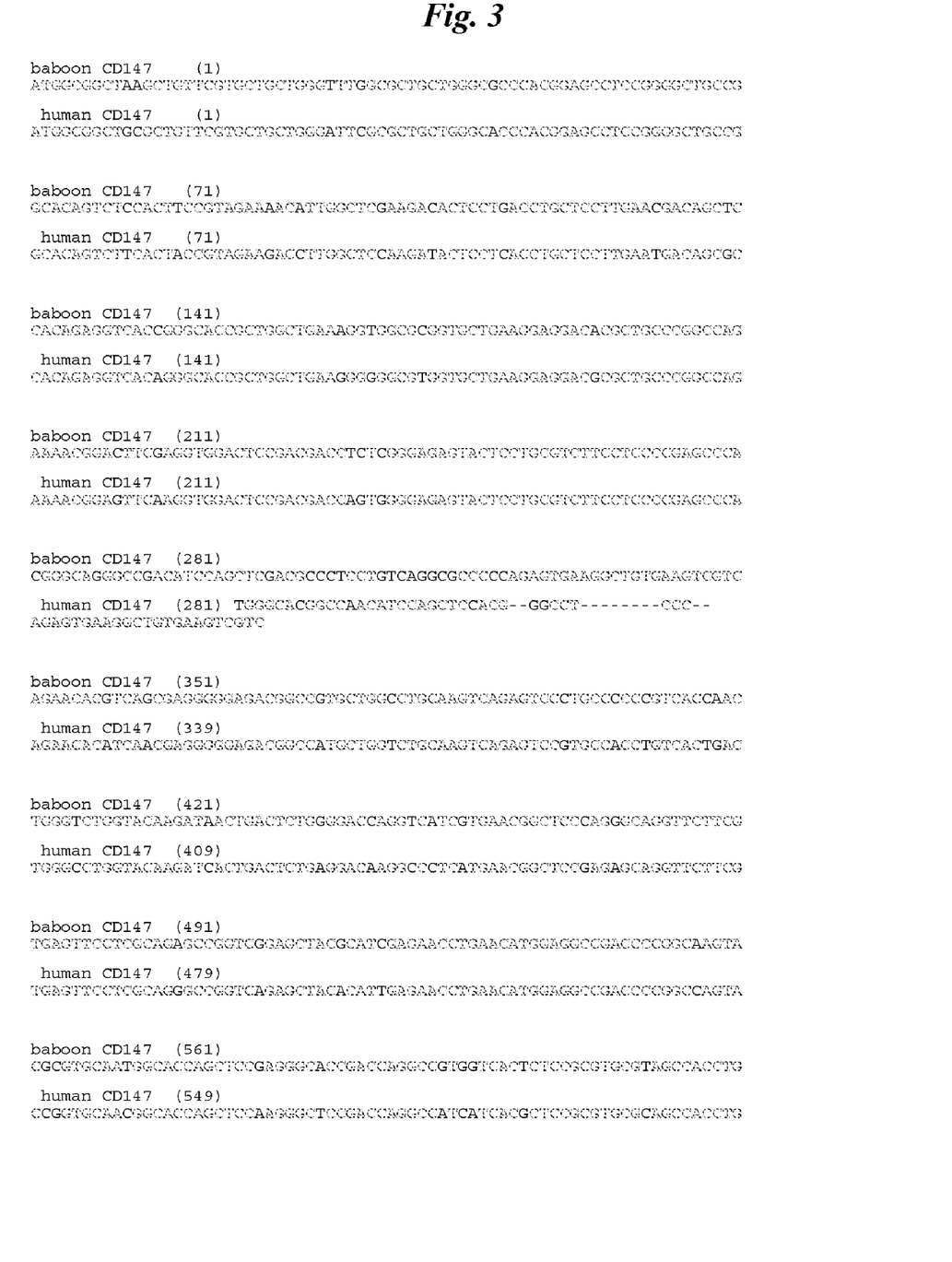
FIG. 3 shows the nucleotide sequence alignment of baboon vs human CD147.

The sequence of baboon CD147 was not available in the public domain. To obtain this information, RNA was isolated from baboon testis and reverse transcribed into a cDNA pool. The baboon CD147 gene was then amplified from this cDNA by RT-PCR and sequenced (SEQ ID NO: 4). The nucleic acid sequences of human (SEQ ID NO: 5) and baboon cDNAs encoding a CD147 isoform 2 were 89% identical (FIG. 3). The sequence of baboon CD147 protein (SEQ ID NO: 6) was found to be 82% identical to the human CD147 protein sequence (SEQ ID NO: 1), and 97% identical to the cynomolgous CD147 protein sequence (SEQ ID NO: 7). Thus, baboon protein divergence from the human sequence is similar to that from cynomolygous suggesting that the baboon may no more relevant as a model for human response in toxicology studies in vivo than is cynomolgous monkey for evaluation of CD147 antagonists, especially antibodies.

Nevertheless, the alignments of primate CD147 amino acid sequences as shown in FIG. 4 including a predicted orangutan sequence (SEQ ID NO: 8), shows that the N-terminal C2-like domain and C-terminal Ig-like are conserved among these proteins although the linking region between the two domains is extended in the two Old World Monkey (baboon and cyno) polypeptides as compared to the hominid (human and orangutan) polypeptides. Oddly, the hominid sequence in this region, GPPR (residues 103-106) is observed to be conserved in homolog proteins from bovine rabbit, Chinese hamster, rat, and mouse (Yu, et al. J Biol Chem 283 (26): 18056-18065, Jun. 27, 2008). Thus, baboon and putative isoform II homolog from Cynomolgus monkey (SEQ ID NO: 7) display a unique difference in this region among the mammalian proteins. The baboon protein exhibits three consensus sites for potential N-glycosylation at asparagines residues 44, 156 and 190.

Compositions

One aspect of the invention is an isolated polynucleotide comprising a polynucleotide having the sequence shown in SEQ ID NO: 4 or a complementary sequence thereof. The polynucleotide sequence shown in SEQ ID NO: 4 encodes a polypeptide comprising the amino acid sequence of SEQ ID NO: 5, representing the precursor sequence of full length baboon CD147. In one aspect of the invention, the polynucleotide is a truncated form of SEQ ID NO: 4 which encodes the mature form of SEQ ID NO: 5 (residues 22-273) such as residues 64-810 of SEQ ID NO: 4. In another aspect, the polynucleotide is a truncated form of SEQ ID NO: 3 comprising nucleotides 1-633 which encodes residues 1-211 (the ECD), or truncated form of SEQ ID NO: 4 comprising nucleotides 1-309 encoding residues 1-103 (the C2-like immunoglobulin domain) of SEQ ID NO: 5. In another aspect, the polynucleotide is a truncated form of SEQ ID NO: 3 comprising nucleotides 325-609 and encoding residues 109-203 (the V-like immunoglobulin domain) of SEQ ID NO: 5.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284, 1989) or the HA peptide tag (Wilson et al., Cell 37:767-778, 1984) which facilitate the purification of fused polypeptides.

Another embodiment of the invention is a vector comprising an isolated polynucleotide having a sequence shown in SEQ ID NO: 4 or truncated forms as described herein.

The vectors of the invention are useful for maintaining polynucleotides, duplicating polynucleotides, or driving expression of a polypeptide encoded by a vector of the invention in a biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids.

The vectors of the invention can be formulated in microparticles, with adjuvants, with lipid, buffer or other excipients as appropriate for a particular application.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art. An exemplary plasmid-derived expression vector useful for expression of the polypeptides of the invention comprises an *E. coli* origin of replication, an aph(3')-1a kanamycin resistance gene, HCMV immediate early promoter with intron A, a synthetic polyA sequence and a bovine growth hormone terminator. Another exemplary plasmid derived expression vector comprises an *E. coli* origin of replication, an ant(4')-1a kanamycin resistance gene, Rous sarcoma virus long terminal repeat sequences, HCMV immediate early promoter and an SV40 late polyA sequence.

Another embodiment of the invention is an isolated host cell comprising a vector of the invention. Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide intact glycosylated proteins include Chinese hamster ovary (CHO) cells, HeLa cells, baby hamster kidney cells (BHK, BHK21, ATCC CRL-10), NSO mouse melanoma cells and derived cell lines, e.g. SP2/0, YB2/0 (ATC CRL-1662) rat myeloma cells, human embryonic kidney cells (HEK, HEK293), human embryonic retina cells PerC.6 cells, hep G2 cells, BSC-1 (e.g., ATCC CRL-26) and many others available from, for example, American Type Culture Collection, Manassas, Va. Populations of cells may comprise an isolated or cultured population of cells or cells present in a matrix such as a tissue.

Mammalian cells such as CHO cells, myeloma cells, cells, BHK cells, mouse Ltk-cells, and NIH3T3 cells have been frequently used for stable expression of heterologous genes. Cell lines such as Cos(COS-1 ATCC CRL 1650; COS-7, ATCC CRL-1651) and HEK293 are routinely used for transient expression of recombinant proteins. A common, preferred bacterial host is *E. coli*.

The polypeptides of the invention may comprise fusion polypeptides comprising a polypeptide of the invention fused with second polypeptide. Such second polypeptides may be leader or secretory signal sequences, a pre- or pro- or preproprotein sequence, as well as naturally occurring, or partially synthetic sequences derived in part from a naturally occurring sequence or an entirely synthetic sequence. Secretory signal or leader polypeptide sequences may be selected to direct secretion of the polypeptides of the invention into the lumen of the endoplasmic reticulum or extracellular environment; such polypeptide sequences may be heterologous or endogenous to any polypeptide from a *Papio* spp. or comprise hybrids of these. Exemplary fusion proteins can be formed by conjugating together a baboon polypeptide having an amino acid sequence shown in SEQ ID NO: 4 and one or more domains derived from or similar to an immunoglobulin domain, such as a CH1 CH2, and CH3 domain. In one aspect, the polypeptide represented by the ECD of SEQ ID NO: 4 (residues 22-203) is fused to an immunoglobulin Fc domain. Such constructs are well known in the art as described in e.g. U.S. Pat. No. 5,116,964, U.S. Pat. No. 5,709,859, U.S. Pat. No. 6,018,026; WO04/002417; WO04/002424; WO05/081687; and WO05/032460. One example of such a related construct is a MIMETIBODY™ construct having the generic formula (I):

$$(V1\text{-}Bp\text{-}Lk\text{-}(V2)_y\text{-}Hg\text{---}C_H2\text{-}C_H3)_{(t)}, \quad (I)$$

where Bp is a peptide or polypeptide capable of binding a molecule of interest, Lk is a polypeptide or chemical linkage, V1 and V2 are portions of an immunoglobulin variable regions, Hg is at least a portion of an immunoglobulin variable hinge region, $C_H2$ is an immunoglobulin heavy chain $C_H2$ constant region and $C_H3$ is an immunoglobulin heavy chain $C_H3$ constant region, y is 0 or 1, and t is independently an integer of 1 to 10.

Another embodiment of the invention is an antibody that specifically binds a polypeptide of the invention. The polypeptides of the invention can be used to produce polyclonal or monoclonal antibodies against baboon CD147. Techniques for making murine, chimeric, humanized and fully human monoclonal antibodies using protein or nucleic acid immunization are routine and well known to those skilled in the art. Additional discussion and description of such techniques can be found herein below.

Methods of Making the Compositions

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR based duplication, vector based duplication, or restriction enzyme based DNA manipulation techniques. Techniques for producing or obtaining polynucleotides of a given known sequence are well known in the art.

Introduction of a polynucleotide, such as a vector, into a host cell can be effected by methods well known to those skilled in the art (Davis et al., Basic Methods in Molecular Biology, 2$^{nd}$ ed., Appleton & Lange, Norwalk, Conn., 1994; Sambrook et al., Molecular Cloning: A Laboratory Manual, 3$^{rd}$ ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lystate based expression systems, wheat germ extract based expression systems, and *Escherichia coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention.

Another embodiment of the invention is a method for expressing a polypeptide comprising the steps of providing a host cell of the invention; culturing the host cell under conditions sufficient for the expression of a polypeptide comprising the sequence shown in SEQ ID NO: 4 or a fragment thereof; and confirming expression of the polypeptide or fragment thereof.

In the methods of the invention, the expression of a polypeptide can be confirmed using a variety of different techniques well known in the art. Detection of the a polypeptide of the expected molecular weight using chromatographic techniques or electrophoretic techniques are well known in the art. In order to confirm that the polypeptide comprise the correct primary, secondary, tertiary or higher order structure other techniques must be employed. For example, expression of a polypeptide can be confirmed using detection reagents, such as antibodies or receptor ligands, specific for an expressed polypeptide. Antibodies that specifically bind to or cross-react with the baboon CD147 polypeptides of the invention are one example of such reagents. Detection reagents may be detectably labeled by conjugation or incorporation of a radiolabel, fluorophore, chromophore or other detectable molecule to, or into, the detection reagent.

Expression of a polypeptide can also be confirmed by assaying for a biological activity associated with CD147, such as increased production of MMPs from fibroblast cultures.

Methods of Using the Invention

In one embodiment of the invention, the isolated polypeptide of SEQ ID NO: 4 or a fragment thereof is used as an immunogen to elicit or "raise" antibodies in a host such as a rabbit, mouse, rat, guinea pig, or goat. In another embodiment, isolated polypeptide of SEQ ID NO: 4 or a fragment thereof may be used to interrogate a library to select molecules capable of binding the polypeptide or fragment thereof. It will be recognized that host cells engineered to with the polynucleotides of SEQ ID NO: 3 or a fragment thereof or a vector comprising such as polynucleotide may also be used for such purposes. In a particularly aspect of using the isolated polypeptide of SEQ ID NO: 4 or a fragment thereof is used to select immunoglobulin fragments from a library of such fragments.

Another embodiment of the invention is a method of determining cross-reactivity of a CD147 modulator with *Papio* spp. baboon CD147. Even if the polypeptides and epitopes are preserved across species and in the species under consideration for a predictive model for a modulator, cross-reactivity of a modulator should be established before additional experimentation is performed (Loisel et al., Crit. Rev. in One.

Hematol. 62:34-42, 2007). Cross-reactivity of modulators, antibodies of the invention and other CD147 antibodies to polypeptides and other antigens may be assayed using for example competitive and non-competitive assay systems using techniques such as BIAcore analysis, FACS, analysis, immunofluorescence, immunocytochemistry, radioimmunoassays, ELISA, "sandwich" immunoassays, immunoprecipitation assays, western blots, immunoradiometric assays, fluorescent immunoassays, and protein A immunoassays. Such assays are routine and well known in the art (Ausubel et al., eds, 1994, Current Protocols in Molecular Biology, Vol. 1, John Wiley & Sons, Inc., New York). Cross-reactivity can also be evaluated by assaying for a biological activity associated with activation of CD147. Additional discussion of such assays can be found above. For example, cross-reactivity of a human anti-CD147 antibody modulator with baboon CD147 polypeptide can be evaluated using assay assessing effect of the antibody on blocking activation of poly(I:C)-induced NF-kB activation downstream of CD147.

Another embodiment of the invention is a method for determining if a CD147 modulator is likely to be safe or unsafe for use in humans comprising providing a CD147 modulator, a first *Papio* spp. baboon, and a second *Papio* spp. baboon; administering the CD147 modulator to the first *Papio* spp. baboon; and determining whether the first *Papio* spp. baboon is presenting a deleterious symptom relative to the second monkey, where presentation of a deleterious symptom by the first *Papio* spp. baboon shows the CD147 modulator is potentially unsafe for use in humans and a lack of presentation of a deleterious symptom by the first *Papio* spp. baboon shows the CD147 therapeutic is potentially safe in humans.

In the methods of the invention the determination of whether the first *Papio* spp. baboon is presenting a deleterious symptom relative to the second *Papio spp. baboon is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, anemia, infections and the like.*

The present invention will now be described with reference to the following specific, non-limiting examples.

EXAMPLE 1

Testis tissue was obtained from a normal *Papio hamadryas* (baboon). The tissue was homogenized mechanically, and subsequently used to prepare total RNA. This RNA was reverse transcribed to generate a cDNA pool.

Figure 1:
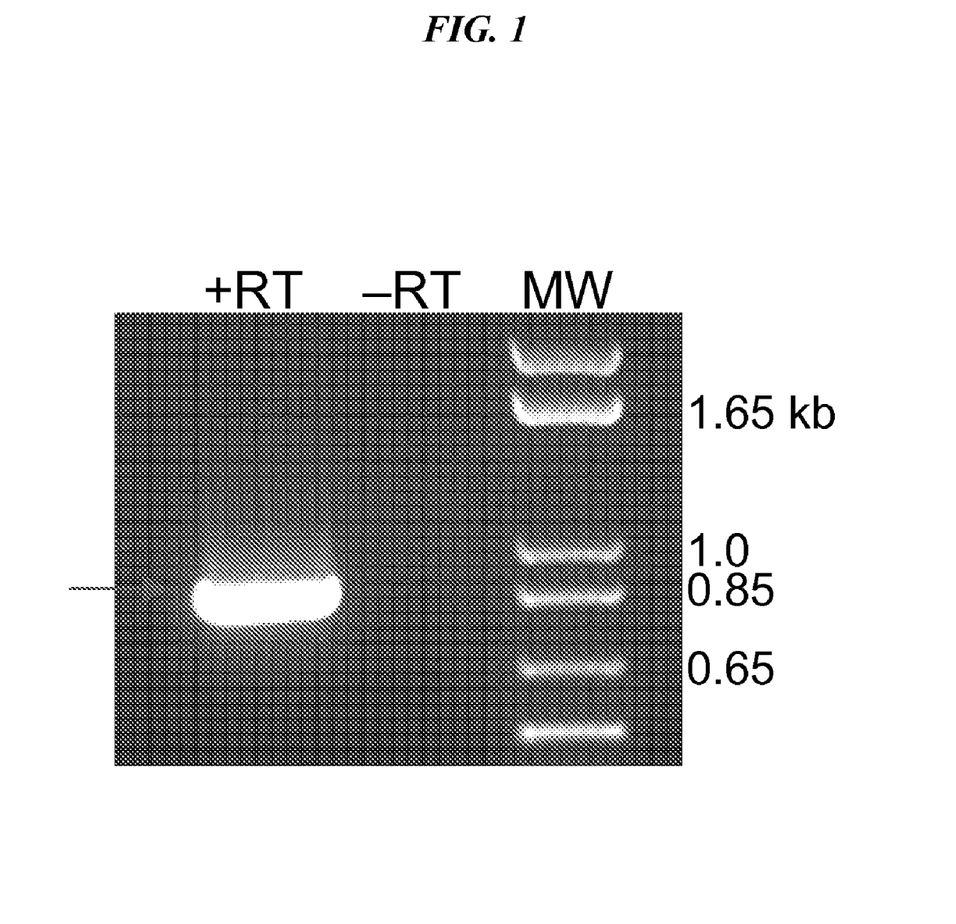
FIG. 1 is an agarose gel electrophoresis showing the separation of PCR products visualized under UV light. A fragment of approximately 810 bp was expected; the band indicated by the red arrow was isolated. (MW=Molecular Weight marker).

The 5' and 3' untranslated regions (UTRs) of the orangutan (*Pongo pygmaeus*) CD147 gene (GenBank accession #CR858460) were used as a template to design PCR primers (Table 1). These primers are also 100% identical to the 5' and 3' UTR of human CD147. Using these oligos, RT-PCR was performed using the baboon testis cDNA pool as a template for amplification. A fragment of approximately 810 bp was expected; the band indicated by the red arrow was isolated. (MW=Molecular Weight marker) in FIG. 1. The fragment was subcloned using the TOPO-TA kit (Invitrogen) (FIG. 1).

TABLE 1

| Description | Oligo sequence | SEQ ID NO: |
|---|---|---|
| 5'UTR CD147 | 5'-CAGGGCCGGCGAGGAGGAGAAATC-3' | 2 |
| 3'UTR CD147 | 5'-GGAGCGTCCTCGGACCACCTGGC-3' | 3 |

Figure 2:
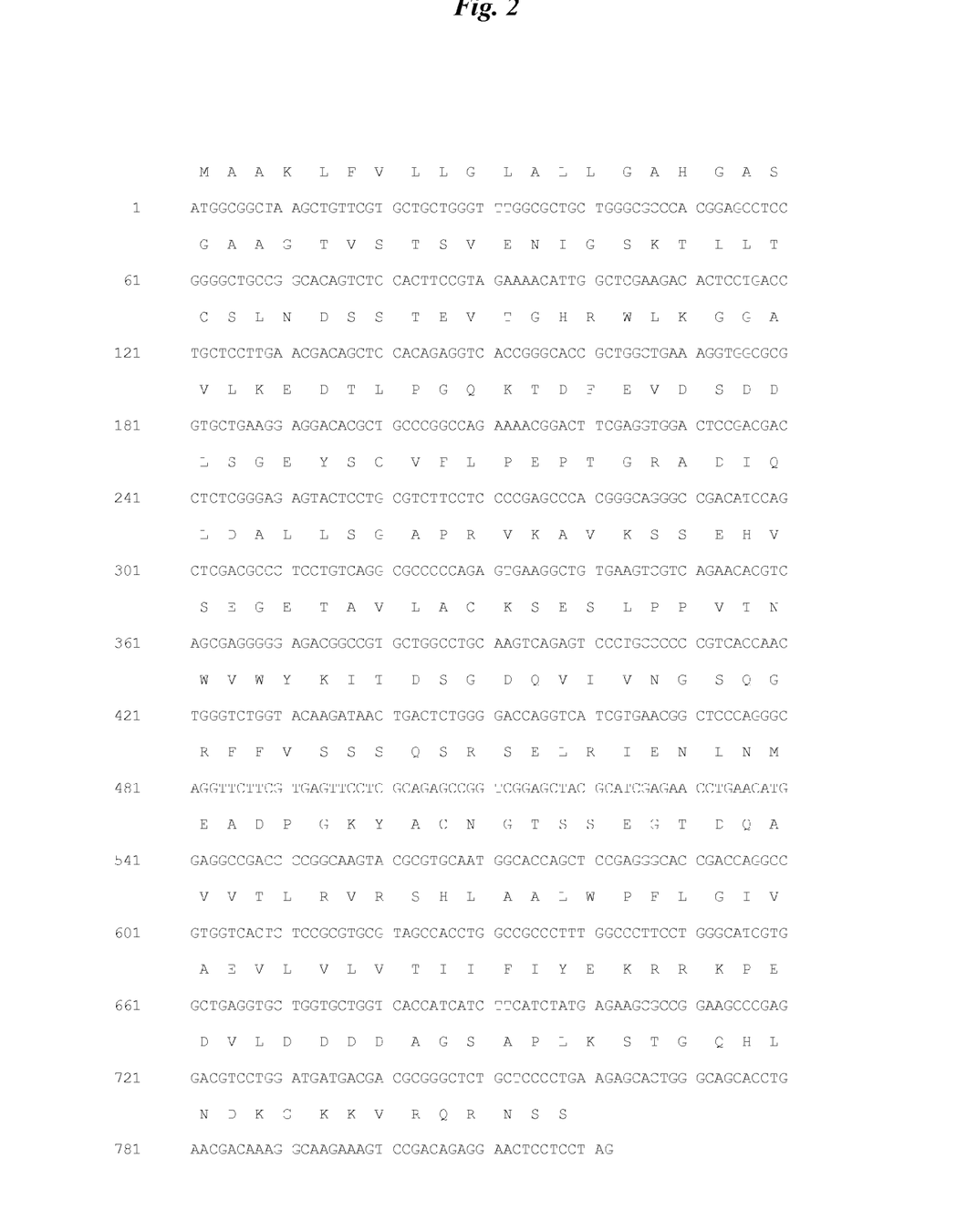
FIG. 2 shows the cDNA sequence of baboon CD147 with the encoded protein sequence shown above the nucleotide which is 82% identical to the human orthologue.

Plasmid DNA from transformants was isolated and sequenced. The confirmed sequence of baboon CD147 cDNA is shown in FIG. 2 (SEQ ID NO: 4) with the translation product (SEQ ID NO: 5). The alignments of baboon and human nucleic acids (FIG. 3) and polypeptides based on human isoform 2 (FIG. 4).

Comparing the discovered baboon protein sequence to that of human, orangutan, and cynomolgus monkey the identities are shown in FIG. 4 produced identity values shown in the table below. It can be seen from the overall identity of amino acids in each position that human and organutan CD147 are closer than are human and baboon CD147. However, unexpectedly, the human sequence is slightly more similar to cynomolgus CD147 than to baboon even though cyno and baboon CD147 are 97.4% identical.

TABLE 1

| Homolog | Baboon Identity | Orangutan | Cyno |
|---|---|---|---|
| human | 81.8% | 88.8% | 82.1% |
| Macaca (cyno) | 97.4% | 89.4% | |
| orangutan | 86.1% | | |

Generally, the primate CD147 molecules have similar structures with the notable difference between the Old World Monkey and Hominid sequences being an additional 4 aa residues inserted between the boundary of the two immunoglobulin-like domains in the extracellular region of the protein. The comparable regions in human CD147 isoform 2 (Accession Record P35613-2) for the baboon polypeptide translation of the cloned cDNA are given in Table 2.

TABLE 2

| | Human Residues (length) | Baboon Residues (length) |
|---|---|---|
| Length | 269 | 273 |
| Signal | 1-21 | 1-21 |
| Extracellular | 22-207 (186) | 22-211 (190) |
| C2-Ig-like domain | 22-103 (82) | 22-103 (82) |
| V-like Ig domain | 105-199 (95) | 109-203 (95) |
| Transmembrane | 208-228 (21) | 212-232 (21) |
| Cytoplasmic | 229-269 (41) | 233-272 (41) |
| N-glycosylation sites | 44, 152, 186 | 44, 156, 190 |

The N-terminal, C2-like Ig domain has been implicated in homodimer formation. A single proline residue separates the C2-like Ig and the V-like Ig domains in the hominid polypeptides while the Old World Monkey polypeptides display a more flexible linkage. Thus, the monkey polypeptides might be expected to engage in three dimensional configurations such as forming higher order complexes between like domains or the two different domains or other molecules not possible for the hominid proteins.

What is to be claimed:

1. An isolated polynucleotide encoding a polypeptide comprising the amino acid sequence shown in SEQ ID NO: 5.

2. The isolated polynucleotide of claim 1 having the sequence shown in SEQ ID NO: 4.

3. A vector comprising an isolated polynucleotide having the sequence shown in SEQ ID NO: 4.

4. The vector of claim 3 that is an expression vector.

5. An isolated host cell comprising the vector of claim 3.

* * * * *

SEQUENCE LISTING

<160> NUMBER OF SEQ ID NOS: 8

<210> SEQ ID NO 1
<211> LENGTH: 269
<212> TYPE: PRT
<213> ORGANISM: Homo sapiens

<400> SEQUENCE: 1

Met Ala Ala Leu Phe Val Leu Leu Gly Phe Ala Leu Leu Gly Thr
1               5                   10                  15

His Gly Ala Ser Gly Ala Ala Gly Thr Val Phe Thr Thr Val Glu Asp
            20                  25                  30

Leu Gly Ser Lys Ile Leu Leu Thr Cys Ser Leu Asn Asp Ser Ala Thr
        35                  40                  45

Glu Val Thr Gly His Arg Trp Leu Lys Gly Gly Val Val Leu Lys Glu
    50                  55                  60

Asp Ala Leu Pro Gly Gln Lys Thr Glu Phe Lys Val Asp Ser Asp Asp
65                  70                  75                  80

Gln Trp Gly Glu Tyr Ser Cys Val Phe Leu Pro Glu Pro Met Gly Thr
                85                  90                  95

Ala Asn Ile Gln Leu His Gly Pro Pro Arg Val Lys Ala Val Lys Ser
            100                 105                 110

Ser Glu His Ile Asn Glu Gly Glu Thr Ala Met Leu Val Cys Lys Ser
        115                 120                 125

Glu Ser Val Pro Pro Val Thr Asp Trp Ala Trp Tyr Lys Ile Thr Asp
    130                 135                 140

Ser Glu Asp Lys Ala Leu Met Asn Gly Ser Glu Ser Arg Phe Phe Val
145                 150                 155                 160

Ser Ser Ser Gln Gly Arg Ser Glu Leu His Ile Glu Asn Leu Asn Met
                165                 170                 175

Glu Ala Asp Pro Gly Gln Tyr Arg Cys Asn Gly Thr Ser Ser Lys Gly
            180                 185                 190

Ser Asp Gln Ala Ile Ile Thr Leu Arg Val Arg Ser His Leu Ala Ala
        195                 200                 205

Leu Trp Pro Phe Leu Gly Ile Val Ala Glu Val Leu Val Leu Val Thr
    210                 215                 220

Ile Ile Phe Ile Tyr Glu Lys Arg Arg Lys Pro Glu Asp Val Leu Asp
225                 230                 235                 240

Asp Asp Asp Ala Gly Ser Ala Pro Leu Lys Ser Ser Gly Gln His Gln
                245                 250                 255

Asn Asp Lys Gly Lys Asn Val Arg Gln Arg Asn Ser Ser
            260                 265

<210> SEQ ID NO 2
<211> LENGTH: 24
<212> TYPE: DNA
<213> ORGANISM: Pongo pygmaeus

<400> SEQUENCE: 2
cagggccggc gaggaggaga aatc                                              24

<210> SEQ ID NO 3
<211> LENGTH: 23
<212> TYPE: DNA
<213> ORGANISM: Pongo pygmaeus

<400> SEQUENCE: 3

```
ggagcgtcct cggaccacct ggc                                              23
```

<210> SEQ ID NO 4
<211> LENGTH: 819
<212> TYPE: DNA
<213> ORGANISM: Papio hamadryas

<400> SEQUENCE: 4

```
atggcggcta agctgttcgt gctgctgggt ttggcgctgc tgggcgccca cggagcctcc      60
ggggctgccg gcacagtctc cacttccgta gaaaacattg gctcgaagac actcctgacc     120
tgctccttga acgacagctc cacagaggtc accgggcacc gctggctgaa aggtggcgcg     180
gtgctgaagg aggacacgct gcccggccag aaaacggact tcgaggtgga ctccgacgac     240
ctctcgggag agtactcctg cgtcttcctc cccgagccca cggcagggc cgacatccag      300
ctcgacgccc tcctgtcagg cgcccccaga gtgaaggctg tgaagtcgtc agaacacgtc     360
agcgagggg agacggccgt gctggcctgc aagtcagagt ccctgccccc cgtcaccaac      420
tgggtctggt acaagataac tgactctggg gaccaggtca tcgtgaacgg ctcccagggc     480
aggttcttcg tgagttcctc gcagagccgg tcggagctac gcatcgagaa cctgaacatg     540
gaggccgacc ccggcaagta cgcgtgcaat ggcaccagct ccgagggcac cgaccaggcc     600
gtggtcactc tccgcgtgcg tagccacctg gccgcccttt ggcccttcct gggcatcgtg     660
gctgaggtgc tggtgctggt caccatcatc ttcatctatg agaagcgccg gaagcccgag     720
gacgtcctgg atgatgacga cgcgggctct gctccctga agagcactgg gcagcacctg      780
aacgacaaag gcaagaaagt ccgacagagg aactcctcc                            819
```

<210> SEQ ID NO 5
<211> LENGTH: 273
<212> TYPE: PRT
<213> ORGANISM: Papio hamadryas

<400> SEQUENCE: 5

```
Met Ala Ala Lys Leu Phe Val Leu Leu Gly Leu Ala Leu Leu Gly Ala
1               5                   10                  15

His Gly Ala Ser Gly Ala Ala Gly Thr Val Ser Thr Ser Val Glu Asn
            20                  25                  30

Ile Gly Ser Lys Thr Leu Leu Thr Cys Ser Leu Asn Asp Ser Ser Thr
        35                  40                  45

Glu Val Thr Gly His Arg Trp Leu Lys Gly Gly Ala Val Leu Lys Glu
    50                  55                  60

Asp Thr Leu Pro Gly Gln Lys Thr Asp Phe Glu Val Asp Ser Asp Asp
65                  70                  75                  80

Leu Ser Gly Glu Tyr Ser Cys Val Phe Leu Pro Glu Pro Thr Gly Arg
                85                  90                  95

Ala Asp Ile Gln Leu Asp Ala Leu Leu Ser Gly Ala Pro Arg Val Lys
            100                 105                 110

Ala Val Lys Ser Ser Glu His Val Ser Glu Gly Glu Thr Ala Val Leu
        115                 120                 125

Ala Cys Lys Ser Glu Ser Leu Pro Pro Val Thr Asn Trp Val Trp Tyr
    130                 135                 140

Lys Ile Thr Asp Ser Gly Asp Gln Val Ile Val Asn Gly Ser Gln Gly
145                 150                 155                 160

Arg Phe Phe Val Ser Ser Ser Gln Ser Arg Ser Glu Leu Arg Ile Glu
                165                 170                 175
```

```
Asn Leu Asn Met Glu Ala Asp Pro Gly Lys Tyr Ala Cys Asn Gly Thr
            180                 185                 190

Ser Ser Glu Gly Thr Asp Gln Ala Val Val Thr Leu Arg Val Arg Ser
        195                 200                 205

His Leu Ala Ala Leu Trp Pro Phe Leu Gly Ile Val Ala Glu Val Leu
    210                 215                 220

Val Leu Val Thr Ile Ile Phe Ile Tyr Glu Lys Arg Arg Lys Pro Glu
225                 230                 235                 240

Asp Val Leu Asp Asp Asp Ala Gly Ser Ala Pro Leu Lys Ser Thr
                245                 250                 255

Gly Gln His Leu Asn Asp Lys Gly Lys Lys Val Arg Gln Arg Asn Ser
            260                 265                 270

Ser

<210> SEQ ID NO 6
<211> LENGTH: 810
<212> TYPE: DNA
<213> ORGANISM: Homo sapiens

<400> SEQUENCE: 6
atggcggctg cgctgttcgt gctgctggga ttcgcgctgc tgggcaccca cggagcctcc      60
ggggctgccg gcacagtctt cactaccgta gaagaccttg ctccaagat actcctcacc     120 tgctccttga atgacagcgc cacagaggtc acaggcacc gctggctgaa ggggggcgtg     180
gtgctgaagg aggacgcgct gcccggccag aaaacggagt tcaaggtgga ctccgacgac     240
cagtggggag agtactcctg cgtcttcctc cccgagccca tgggcacggc caacatccag     300
ctccacgggc tcccagagt gaaggctgtg aagtcgtcag aacacatcaa cgaggggag     360 acggccatgc tggtctgcaa gtcagagtcc gtgccacctg tcactgactg ggcctggtac     420
aagatcactg actctgagga caaggccctc atgaacggct ccgagagcag gttcttcgtg     480
agttcctcgc agggccggtc agagctacac attgagaacc tgaacatgga ggccgacccc     540
ggccagtacc ggtgcaacgg caccagctca aagggctccg accaggccat catcacgctc     600
cgcgtgcgca gccacctggc cgccctctgg cccttcctgg gcatcgtggc tgaggtgctg     660
gtgctggtca ccatcatctt catctacgag aagcgccgga agcccgagga cgtcctggat     720
gatgacgacg ccggctctgc acccctgaag agcagcgggc agcaccagaa tgacaaaggc     780
aagaacgtcc gccagaggaa ctcttcctga                                       810

<210> SEQ ID NO 7
<211> LENGTH: 273
<212> TYPE: PRT
<213> ORGANISM: Macaca fascicularis

<400> SEQUENCE: 7

Met Ala Ala Ala Leu Phe Val Leu Leu Gly Leu Ala Leu Gly Ala
1               5                   10                  15

His Gly Ala Tyr Gly Ala Ala Gly Thr Val Ser Thr Val Glu Asn
                20                  25                  30

Ile Gly Ser Lys Thr Leu Leu Thr Cys Ser Leu Asn Asp Ser Ser Thr
            35                  40                  45

Glu Val Thr Gly His Arg Trp Leu Lys Gly Gly Ala Val Leu Lys Glu
        50                  55                  60

Asp Thr Leu Pro Gly Gln Lys Thr Asp Phe Glu Val Asp Ser Asp
65                  70                  75                  80

Leu Gly Gly Glu Tyr Ser Cys Val Phe Leu Pro Glu Pro Thr Gly Arg
```

```
                        85                  90                  95
Ala Asp Ile Gln Leu Asp Ala Val Leu Ser Gly Ala Pro Arg Val Lys
                100                 105                 110
Ala Val Lys Ser Ser Glu His Val Ser Glu Gly Glu Thr Ala Val Leu
            115                 120                 125
Ala Cys Lys Ser Glu Ser Leu Pro Pro Val Thr Thr Trp Val Trp Tyr
        130                 135                 140
Lys Ile Thr Asp Ser Gly Asp Gln Val Ile Val Asn Gly Ser Gln Gly
145                 150                 155                 160
Arg Phe Phe Val Ser Ser Ser Gln Gly Arg Ser Glu Leu Arg Ile Glu
                165                 170                 175
Asn Leu Asn Met Glu Ala Asp Pro Gly Lys Tyr Ala Cys Asn Gly Thr
            180                 185                 190
Ser Ser Glu Gly Thr Asp Gln Ala Thr Val Thr Leu Arg Val Arg Ser
        195                 200                 205
His Leu Ala Ala Leu Trp Pro Phe Leu Gly Ile Val Ala Glu Val Leu
    210                 215                 220
Val Leu Val Thr Ile Ile Phe Ile Tyr Glu Lys Arg Arg Lys Pro Glu
225                 230                 235                 240
Asp Val Leu Asp Asp Asp Ala Gly Ser Ala Pro Leu Lys Ser Thr
                245                 250                 255
Gly Gln His Leu Asn Asp Lys Gly Lys Lys Val Arg Gln Arg Asn Ser
            260                 265                 270
Ser

<210> SEQ ID NO 8
<211> LENGTH: 269
<212> TYPE: PRT
<213> ORGANISM: Pongo abelii
<300> PUBLICATION INFORMATION:
<308> DATABASE ACCESSION NUMBER: NP_001128860
<309> DATABASE ENTRY DATE: 2008-09-28
<313> RELEVANT RESIDUES IN SEQ ID NO: (1)..(269)

<400> SEQUENCE: 8

Met Ala Ala Ala Leu Phe Val Leu Leu Gly Phe Ala Leu Leu Gly Thr
1               5                   10                  15
His Gly Ala Ser Gly Ala Ala Gly Thr Val Phe Thr Thr Val Glu Asp
                20                  25                  30
Leu Gly Ser Lys Ile Leu Leu Thr Cys Ser Leu Asn Asp Ser Ala Thr
            35                  40                  45
Glu Val Thr Gly His Arg Trp Leu Lys Gly Gly Val Val Leu Lys Glu
        50                  55                  60
Asp Ala Leu Pro Gly Gln Lys Thr Glu Phe Lys Val Asp Ser Asp Asp
65                  70                  75                  80
Gln Trp Gly Glu Tyr Ser Cys Val Phe Leu Pro Glu Pro Met Gly Thr
                85                  90                  95
Ala Asn Ile Gln Leu His Gly Pro Pro Arg Val Lys Ala Val Lys Ser
                100                 105                 110
Ser Glu His Ile Asn Glu Gly Glu Thr Ala Met Leu Val Cys Lys Ser
            115                 120                 125
Glu Ser Val Pro Pro Val Thr Asp Trp Ala Trp Tyr Lys Ile Thr Asp
        130                 135                 140
Ser Glu Asp Lys Ala Leu Met Asn Gly Ser Glu Ser Arg Phe Phe Val
145                 150                 155                 160
Ser Ser Ser Gln Gly Arg Ser Glu Leu His Ile Glu Asn Leu Asn Met
```

-continued

```
            165                 170                 175
Glu Ala Asp Pro Gly Gln Tyr Arg Cys Asn Gly Thr Ser Ser Lys Gly
            180                 185                 190

Ser Asp Gln Ala Ile Ile Thr Leu Arg Val Arg Ser His Leu Ala Ala
            195                 200                 205

Leu Trp Pro Phe Leu Gly Ile Val Ala Glu Val Leu Val Leu Val Thr
            210                 215                 220

Ile Ile Phe Ile Tyr Glu Lys Arg Arg Lys Pro Glu Asp Val Leu Asp
225                 230                 235                 240

Asp Asp Asp Ala Gly Ser Ala Pro Leu Lys Ser Ser Gly Gln His Gln
            245                 250                 255

Asn Asp Lys Gly Lys Asn Val Arg Gln Arg Asn Ser Ser
            260                 265
```